US006150329A

United States Patent [19]
Dean et al.

[11] Patent Number: 6,150,329
[45] Date of Patent: Nov. 21, 2000

[54] MULTIMERIC ANTITHROMBOTIC AGENTS

[75] Inventors: Richard T. Dean; John Lister-James, both of Bedford, N.H.

[73] Assignee: Diatide, Inc., Londonderry, N.H.

[21] Appl. No.: 08/466,290

[22] Filed: Jun. 6, 1995

Related U.S. Application Data

[62] Division of application No. 08/361,864, Dec. 22, 1994, Pat. No. 5,977,064, which is a continuation of application No. 07/955,466, Oct. 2, 1992, abandoned, which is a continuation-in-part of application No. 07/893,981, Jun. 5, 1992, Pat. No. 5,508,020.

[51] Int. Cl.$^7$ .......................... A61K 38/00; A61K 38/02
[52] U.S. Cl. ............................. 514/12; 514/17; 514/18; 514/19
[58] Field of Search ................................. 514/12, 17, 18, 514/19; 530/301–324

[56] References Cited

U.S. PATENT DOCUMENTS

| | | |
|---|---|---|
| 4,578,079 | 3/1986 | Ruoslathi et al. . |
| 4,614,517 | 9/1986 | Ruoslahti et al. ...................... 530/300 |
| 4,792,525 | 12/1988 | Ruoslahti et al. . |
| 4,952,562 | 8/1990 | Klein et al. . |
| 5,185,433 | 2/1993 | Dean et al. ........................... 530/391.1 |
| 5,338,725 | 8/1994 | Ojima et al. .............................. 514/13 |
| 5,508,020 | 4/1996 | Dean et al. .............................. 530/300 |

FOREIGN PATENT DOCUMENTS

| | | |
|---|---|---|
| 410537 | 1/1991 | European Pat. Off. . |
| 410539 | 1/1991 | European Pat. Off. . |
| 410540 | 1/1991 | European Pat. Off. . |
| 410541 | 1/1991 | European Pat. Off. . |
| 422937 | 4/1991 | European Pat. Off. . |
| 422938 | 4/1991 | European Pat. Off. . |
| 425212 | 5/1991 | European Pat. Off. . |
| 446071 | 9/1991 | European Pat. Off. . |
| 482649 | 4/1992 | European Pat. Off. . |
| 503301 | 9/1992 | European Pat. Off. . |
| WO8905150 | 6/1989 | WIPO . |
| WO8910135 | 11/1989 | WIPO . |
| WO9006767 | 6/1990 | WIPO . |
| WO9101331 | 2/1991 | WIPO . |
| WO9102750 | 3/1991 | WIPO . |
| WO9115515 | 10/1991 | WIPO . |
| WO9117173 | 11/1991 | WIPO . |
| WO9407918 | 4/1994 | WIPO . |

OTHER PUBLICATIONS

Ojima et al., ., "Design and Synthesis of New RGD Peptides as Inhibitors of Human Platelet Aggregation," 204$^{th}$ Meeting, Amer. Chem. Soc. Abst. 44 1992.

Zucker, "Platelet Aggregation Measured by the Photometric Method," Methods in Enzymol. 169:117–133 (1989).

Cheronis et al., "A New Class of Bradykinin Antagonists; synthesis and in vitro activity of bissuccinimidoalkane peptide dimers," Journal of Medicinal Chemistry 35(9):1563–1572 (May 1, 1992).

Hruby et al., "Conformational Restrictions of Biologically Alive Peptides Via Amino Acid Side Chain Groups," Life Sciences 31(3):189–199 (Jul. 19, 1982).

Pierschbacher and Ruoslahti, "Influence of Stereochemistry of the Sequence Arg–Gly–Asp–Xaa on Binding Specificity in Cell Adhesion," The Journal of Biological Chemistry 262(36):17294–17298 (Dec. 25, 1987).

Tjoeng et al., "Peptide mimetics of the RGD sequence," Proceedings of the 12$^{th}$ American Peptide Symposium, held in Cambridge, MA on Jun. 16–21, 1991, Abst. LTh8.

Burnier et al., "Small cyclic RGD containing peptides as potent inhibitors of platelet aggregation," Proceedings of the 12$^{th}$ American Peptide Symposium, held in Cambridge, MA on Jun. 16–21, 1991, Abst. LTh9.

Ali et al., "Potent fibrinogen receptor antagonists bearing conformational constraints," Proceedings of the 12$^{th}$ American Peptide Symposium, held in Cambridge, MA on Jun. 16–21, 1991, Abst. P–471.

Brady et al., "Large–scale synthesis of L–367,073, a potent cyclic heptapeptide platelet fibrinogen receptor antagonist," Proceedings of the 12$^{th}$ American Peptide Symposium, held in Cambridge, MA on Jun. 16–21, 1991, p. 657.

Caulfield et al., "A novel calciotrophic hormone, parathyriod hormone–related protein, biology and structure/function studies," Proceedings of the 12$^{th}$ American Peptide Symposium, held in Cambridge, MA on Jun. 16–21, 1991, p. 902.

Nutt et al., "Development of novel, highly selective fibrinogen receptor antagonists as potentially useful antithrombotic agents," Proceedings of the 12$^{th}$ American Peptide Symposium, held in Cambridge, MA on Jun. 16–21, 1991, p. 914.

Chong et al., "Mapping of the immunodominant B–and T–cell epitopes of the outer membrane protein P1 of H. influenzae type b using overlapping synthetic peptides," Proceedings of the 12$^{th}$ American Peptide Symposium, held in Cambridge, MA on Jun. 16–21, 1991, p. 697.

Primary Examiner—Avis M. Davenport
Attorney, Agent, or Firm—Patricia A. McDaniels; Kevin Noonan

[57] ABSTRACT

This invention relates to antithrombotic agents and uses thereof. Specifically, the invention relates to chemical moieties that specifically bind to platelets and inhibit their aggregation, including linear and cyclic peptides. The invention provides methods for using these antithrombotic agents to prevent the formation of thrombi at sites in a mammalian body. In particular, the platelet-specific binding moieties including linear and cyclic peptides of the invention are covalently linked to a polyvalent linker moiety, so that the polyvalent linker moiety is covalently linked to a multiplicity of the platelet-specific binding moieties including linear and cyclic peptides. Effficacious antithrombotic agents are thereby provided.

7 Claims, No Drawings

MULTIMERIC ANTITHROMBOTIC AGENTS

This application is a divisional of U.S. patent application Ser. No. 08/361,864, filed Dec. 22, 1994 now U.S. Pat. No. 5,977,064; which is a continuation of U.S. patent application Ser. No. 07/955,466, filed Oct. 2, 1992 and now abandoned; this application is also a continuation-in-part of U.S. patent application Ser. No. 07/893,981, filed Jun. 5, 1992 and now U.S. Pat. No. 5,508,020.

BACKGROUND OF THE INVENTION

1. Field of the Invention

This invention relates to antithrombotic agents and uses thereof. Specifically, the invention relates to compounds that bind to platelets, specifically compounds that bind to the platelet receptor molecule GPIIb/IIIa. Such compounds include peptides and cyclic peptides that bind to platelets and inhibit their aggregation. In particular, the platelet-specific antithrombotic agents of the invention are covalently linked to a polyvalent linker moiety, so that the polyvalent linker moiety is covalently linked to a multiplicity of the platelet-specific moieties, particularly peptides and cyclic peptides, thereby providing the multimeric polyvalent antithrombotic agents of the invention. The invention also provides methods for using such compounds to prevent the formation of thrombi at sites in a mammalian body.

2. Description of the Prior Art

Thrombosis and thromboembolism, in particular deep vein thrombosis (DVT) and pulmonary embolism (PE), are common clinical conditions that are associated with significant morbidity and mortality. It has been estimated that in the U.S. approximately 5 million patients experience one or more episodes of DVT per year and that over 500,000 cases of pulmonary embolism occur, resulting in 100,000 deaths (J. Seabold, Society of Nuclear Medicine Annual Meeting 1990).

In addition, myocardial infarction (heart attack) is usually caused by thrombosis in a coronary artery, often at the site of an atheroschlerotic plaque. Conventional therapies for heart attack involve removing such thrombi, either surgically by angioplasty and/or by adminstration of thrombolytic drugs, such as recombinant tissue plasminogen activator or streptokinase. Following such therapy, however, re-stenosis or even re-occlusion of the affected coronary artery frequently occurs due to formation of another thrombus at the site of the original thrombus. Preventing such re-occurrence of coronary artery thrombi is thus an important goal of all post-infarct therapy.

The physiological processes involved in the formation of thrombi are initiated by the accumulation of platelets at sites of damage or insult to the endothelial cell wall of a blood vessel, such as an atheroschlerotic plaque. Platelets normally accumulate at such sites after stimulation by local mediators signalling the injury. Subsequently, such platelets become aggregated at such sites by binding serum fibrinogen via GPIIb/IIIa receptors expressed on the platelet surface. It is with the binding of fibrinogen that such an aggregation of platelets becomes a thrombus.

The amino acid sequence of the fibrinogen molecule recognized by GPIIb/IIIa receptors is the sequence -Arg-Gly-Asp- (RGD), which sequence is present four times in each fibrinogen molecule. Platelet aggregation can be inhibited using fibrinogen antagonists that bind to the GPIIb/IIIa receptors. Thus, compounds that are fibrinogen antagonists and bind to GPIIb/IIIa are useful in preventing thrombosis, particularly in post-angioplasty or post-thrombolytic treatment regimes.

Peptides having the ability to bind to platelets and inhibit their aggregation are known in the prior art.

Ruoslahti & Pierschbacher, U.S. Pat. No. 4,578,079 describe peptides of sequence X-Arg-Gly-Asp-R-Y, wherein X and Y are either H or an amino acid, and R is Thr or Cys, the peptides being capable of binding to platelets.

Ruoslahti & Pierschbacher, U.S. Pat. No. 4,792,525 describe peptides of sequence Arg-Gly-Asp-X, wherein X is Ser, Thr or Cys, the peptides being capable of binding to platelets.

Pierschbacher et al., 1989, PCT/US88/04403 disclose conformationally-restricted RGD-containing peptides for inhibiting cell attachment to a substratum.

Hawiger et al., 1989, PCT/US89/01742 relates to peptides comprising sequences for two binding sites of a protein.

Nutt et al., 1990, European Patent Application 90202015.5 disclose cyclic RGD peptides that are fibrinogen receptor antagonists.

Nutt et al., 1990, European Patent Application 90202030.4 disclose cyclic RGD peptides that are fibrinogen receptor antagonists.

Nutt et al., 1990, European Patent Application 90202031.2 disclose cyclic RGD peptides that are fibrinogen receptor antagonists.

Nutt et al., 1990, European Patent Application 90202032.0 disclose cyclic RGD peptides that are fibrinogen receptor antagonists.

Nutt et al., 1990, European Patent Application 90311148.2 disclose cyclic peptides that are fibrinogen receptor antagonists.

Nutt et al., 1990, European Patent Application 90311151.6 disclose cyclic peptides that are fibrinogen receptor antagonists.

Ali et al., 1990, European Patent Application 90311537.6 disclose cyclic peptides that are fibrinogen receptor antagonists.

Barker et al., 1991, PCT/US90/03788 disclose cyclic peptides for inhibiting platelet aggregation.

Maraganore et al., 1991, PCT/US90/04642 disclose a radiolabeled thrombus inhibitor comprising (a) an inhibitor moiety; (b) a linker moiety; and (c) and an "anion binding exosite (ABE)" binding site moiety.

Pierschbacher et al., 1991, PCT/US91/02356 disclose cyclic peptides that are fibrinogen receptor antagonists.

Ojima et al., 1992, 204th Meeting, Amer. Chem. Soc. Abst. 44 disclose synthetic multimeric RDGF peptides useful in inhibiting platelet aggregation.

Although it is possible to prepare cyclic peptides that specifically bind to platelets, some such peptides exhibit low binding site affinity whereby the strength of peptide binding to platelets is insufficient to prevent platelet aggregation and thereby have an antithrombotic effect. Peptides comprised of linear arrays of thrombus-specific peptide binding units have been described in the prior art.

Rodwell et al., 1991, PCT/US91/03116 disclose linear arrays of the peptide sequence RGD.

Alternative arrangements of specific binding peptide units are preferable. The present invention provides multimeric polyvalent antithrombotic agents, one embodiment of which is a reagent comprised of a multiplicity of cyclic peptides that specifically bind to platelets and have a sufficient affinity for platelets to prevent their aggregation. The incorporation of a multiplicity of platelet-specific cyclic peptides in the antithrombotic agents of the invention permits the use of particular platelet-specific cyclic peptides comprising platelet binding sequences whose individual binding affinity might not otherwise be sufficient to produce the desired inhibition of platelet aggregation resulting in an antithrombotic effect in vivo, but which have other desireable properties, such as improved in vivo stability and half-life, which are evidenced for example by increased retention times at thrombus sites in vivo, detected by Tc-99m scintigraphy. Improved inhibition of platelet aggregation by particular platelet-specific binding moieties including peptides and cyclic peptides is achieved using the multimeric polyvalent antithrombotic agents of this invention.

SUMMARY OF THE INVENTION

The present invention provides multimeric polyvalent antithrombotic agents useful for preventing thrombus formation in a mammalian body.

In a first aspect, the invention provides a multimeric polyvalent antithrombotic agent comprising a multiplicity of platelet-binding moieties that are ligands for a platelet GPIIb/IIIa receptor molecule, covalently linked to a polyvalent linking moiety. In a preferred embodiment, such a multimeric polyvalent antithrombotic agent has a molecular weight of less than about 20,000 daltons.

In a second aspect, the invention provides a multimeric polyvalent antithrombotic agent comprising a multiplicity of platelet binding peptides, each peptide comprising an amino acid sequence of 3–100 amino acids, covalently linked to a polyvalent linking moiety, wherein each of the platelet binding peptides has the formula A-Y-X-Gly-Asp-(aa)$_n$-Z-B wherein A is H, an amine protecting group or (aa)$_p$, where (aa) is any amino acid, wherein when the amino acid is cysteine, said cysteine may be protected at its sidechain sulfur atom and p is an integer from 0 to 97; Y is a lipophilic amino acid or H; X is an amino acid capable of being positively charged; (aa) is any amino acid, wherein when the amino acid is cysteine, said cysteine may be protected at its sidechain sulfur atom and n is an integer from 0 to 97; Z is either absent or cysteine, isocysteine or homocysteine; B is —OH, —NH$_2$, —SH or (aa)$_m$, wherein (aa) is any amino acid, wherein when the amino acid is cysteine, said cysteine may be protected at its sidechain sulfur atom, and m is an integer from 0 to 94; and the sum of n+m+p is less than or equal to 97. In a preferred embodiment, the lipophilic amino acid is a phenylalanine, tyrosine, tryptophan, valine, leucine or isoleucine residue. Lysine, homolysine, arginine, homoarginine, or L-[S-(3-aminopropyl)cysteine are preferred as amino acid X in the formula. Each of the multiplicity of platelet binding peptides is preferably comprised of 3 to 20 amino acids.

In another aspect, the invention provides multimeric polyvalent antithrombotic agents, each comprising a multiplicity of platelet binding cyclic peptides, each peptide comprising an amino acid sequence of 5–100 amino acids, covalently linked to a polyvalent linking moiety, wherein each of the platelet binding cyclic peptides has the formula

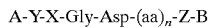

CH$_2$—CO—Y$_D$-X-Gly-Asp-Cys-(aa)$_n$-Z-B wherein Y$_D$ is a lipophilic amino acid; X is an amino acid capable of being positively charged; (aa) is any amino acid, wherein when the amino acid is cysteine, said cysteine may be protected at its sidechain sulfur atom; n is an integer from 0 to 95; Z is either absent or cysteine, isocysteine or homocysteine; and B is —OH, —NH$_2$, —SH, or (aa)$_m$, wherein (aa) is any amino acid, wherein when the amino acid is cysteine, said cysteine may be protected at its sidechain sulfur atom, m is an integer from 0 to 95, and the sum of n+m is $\leq 95$. In a preferred embodiment, the lipophilic D-amino acid is selected from the group consisting of phenylalanine, tyrosine, tryptophan, valine, leucine and isoleucine. Lysine, homolysine, arginine, homoarginine, or L-[S-(3-aminopropyl)cysteine are preferred as amino acid X in the formula. In another preferred embodiment, each of the multiplicity of platelet binding cyclic peptides is comprised of 5 to 20 amino acids.

The invention also provides a multimeric polyvalent antithrombotic agent comprising a multiplicity of platelet binding peptides, each peptide comprising an amino acid sequence of 3–100 amino acids, covalently linked to a polyvalent linking moiety, wherein each of the platelet binding peptides has the formula A—Y-X-Gly-Asp-(R)-Z-B wherein A is H, an amine protecting group or (aa)$_p$, where (aa) is any amino acid, wherein when the amino acid is cysteine, said cysteine may be protected at its sidechain sulfur atom, and p is an integer from 0 to 97; Y is a lipophilic amino acid or H; X is an amino acid capable of being positively charged; (R) is a substituted or unsubstituted linear or branched chain lower alkyl group having 1–20 carbon atoms or a substituted or unsubstituted phenyl, aryl, polycyclic or heterocyclic group, optionally comprising at least one heteroatom selected from the group consisting of O, S, and N; Z is either absent or cysteine, isocysteine or homocysteine; and B is —OH, —NH$_2$, —SH, or (aa)$_m$, wherein (aa) is any amino acid, wherein when the amino acid is cysteine, said cysteine may be protected at its sidechain sulfur atom, and m is an integer from 0 to 97; and the sum of m+p is less than or equal to 97. In a preferred embodiment, the lipophilic amino acid is selected from the group consisting of phenylalanine, tyrosine, tryptophan, valine, leucine and isoleucine. Lysine, homolysine, arginine, homoarginine, or L-{S-(3-aminopropyl)cysteine} are preferred as amino acid X in the formula. In another preferred embodiment, each of the multiplicity of platelet binding cyclic peptides is comprised of 3 to 20 amino acids.

In yet another aspect, the invention provides multimeric polyvalent antithrombotic agents, each comprising a multiplicity of platelet binding cyclic peptides, each peptide comprising an amino acid sequence of 5–100 amino acids, covalently linked to a polyvalent linking moiety, wherein each of the platelet binding cyclic peptides has the formula

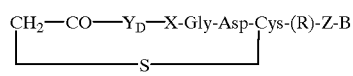

CH$_2$—CO—Y$_D$—X-Gly-Asp-Cys-(R)-Z-B
|_____S_____| wherein Y$_D$ is a lipophilic D-amino acid; X is an amino acid capable of being positively charged; (R) is a substituted or unsubstituted linear or branched chain lower alkyl group having 1 to 20 carbon atoms, or a substituted or unsubstituted phenyl, aryl, polycyclic or heterocyclic group optionally comprising at least one heteroatom selected from the group consisting of O, S, and N; Z is either absent or cysteine, isocysteine or homocysteine; and B is —OH, —NH$_2$, —SH, or (aa)$_m$, wherein (aa) is any amino acid, wherein when the amino acid is cysteine, said cysteine may be protected at its sidechain sulfur atom, and m is an integer from 0 to 95. In a preferred embodiment, the lipophilic D-amino acid is selected from the group consisting of phenylalanine, tyrosine, tryptophan, valine, leucine and isoleucine. Lysine, homolysine, arginine, homoarginine, or L-[S-(3-aminopropyl)cysteine are preferred as amino acid X in the formula. In another preferred embodiment, each of the multiplicity of platelet binding cyclic peptides is comprised of 5 to 20 amino acids.

In each of the linear peptides comprising a multimeric polyvalent antithrombotic agent of the invention the amino terminus may be protected by an amine protecting group. Preferred amine protecting groups include but are not limited to aliphatic or aromatic acyl groups comprising lower alkyl having 1 to 6 carbon atoms, or phenyl or phenyl substituted with lower alkyl, hydroxy, lower alkoxy, carboxy, or lower alkoxycarbonyl groups.

In each of the cyclic peptides of the invention having an amino acid residue (aa) comprising a cysteine, the sulfur atom of such a cysteine residue may be protected by a thiol protecting group. Preferably, such thiol protecting groups have the formula

—CH$_2$—NH—CO—R wherein R is a lower alkyl having 1 to 6 carbon atoms, 2-,3-,4-pyridyl, phenyl, or phenyl substituted with lower alkyl, hydroxy, lower alkoxy, carboxy, or lower alkoxycarbonyl.

The multimeric polyvalent antithrombotic agents of the invention comprise polyvalent linking moieties. Such polyvalent linking moieties are comprised of at least 2 linker functional groups capable of covalently bonding to the platelet binding moieties and linear and cyclic peptides comprising the antithrombotic agents of the invention. Preferably, at least 2 of the linker functional groups are identical, and most preferably, the linker functional groups are primary or secondary amines, hydroxyl groups, carboxylic acid groups or thiol-reactive groups. In a preferred embodiment, the polyvalent linking moieties are comprised of a multiplicity of polyvalent linking moieties covalently linked to form a branched polyvalent linkng moiety. Preferred polyvalent linking moieties are bis-succinimidylmethylether, tris(succinimidylethyl)amine and derivatives thereof.

Platelet-binding peptides provided by the invention include but are not limited to peptides comprising the following sequences, including the following cyclic peptides:

<u>CH$_2$CO.Y$_D$RGDC</u>
<u>CH$_2$CO.Y$_D$RGDCWGG</u>
<u>CH$_2$CO.Y$_D$RGDCFGG</u>
<u>CH$_2$CO.Y$_D$RGDCGGG</u>
<u>CH$_2$CO.Y$_D$RGDCGG</u>
<u>CH$_2$CO.Y$_D$.Apc.GDCGGG</u>
<u>CH$_2$CO.Y$_D$KGDCGGG</u>
<u>GGCNP.Apc.GDC</u>
GGRGDS
GGRGDGGRGDS
GGRGDGGRGDGGRGDS
KRARGDDMDDY
RRRRRRRRRGD
GRGDVK
GRGDV
GRGDVRGDFK
GRGDVRGDF
GGGRGDF
<u>NP.Apc.GD</u>
RGD
GRGDGG
GGRGDF
GGGRGDF
GRGDGGGG
RGDF
<u>G.Apc.GDV.Apc.GD</u>FKCamide
<u>SYNRGDSTC</u>
<u>CH$_2$CO.Y$_D$.Apc.GDCGGC$_{Acm}$GC$_{Acm}$GG</u>Camide Single-letter abbreviations for amino acids can be found in G. Zubay, *Biochemistry* (2d. ed.), 1988 (MacMillen Publishing: New York) p.33. It will be understood by those with skill in the art that the sequences underlined in the above structures and in all other structures included herein represent a covalent bond between the the first and the last so underlined molecules, and further that when cysteine is either the first or the last underlined molecule, such a covalent bond will be to the sidechain sulfer atom of said cysteine.

This invention provides methods for preparing peptides of the invention by chemical synthesis in vitro. In a preferred embodiment, peptides are synthesized by solid phase peptide synthesis.

The invention also provides a method for preventing thrombosis within a mammalian body. This method comprises administering an effective therapeutic amount of a multimeric polyvalent antithrombotic agent of the invention to an animal in a pharmaceutical carrier.

Specific preferred embodiments of the present invention will become evident from the following more detailed description of certain preferred embodiments and the claims.

DETAILED DESCRIPTION OF THE INVENTION

The present invention provides multimeric, polyvalent compounds which inhibit platelet aggregation and thus exhibit antithrombotic properties in a mammalian body, comprising a multiplicity of platelet-specific binding moieties, including peptides and cyclic peptides having an amino acid sequence of 3–100 amino acids, covalently linked to a polyvalent linking moiety.

For purposes of this invention, the term "multimeric" is defined to describe compounds having multiple copies of a platelet-binding moeity that is a ligand for a platelet GPIIb/IIIa receptor molecule. Exemplary of such platelet binding moieties are peptides and cyclic peptides having an amino acid sequence comprising the sequence -Arg-Gly-Asp- (RGD), in linear or polyvalent arrays. For the purposes of this invention, the term "polyvalent" is defined to describe compounds in which a multiplicity of platelet-specific binding moieties, including peptides and cyclic peptides having an amino acid sequence having specific platelet-binding properties, exemplified by the sequence -Arg-Gly-Asp- (RDG), are covalently linked to a moiety having at least 2 functional groups, each capable of covalent linkage to platelet-binding moieties of the invention.

The polyvalent multimeric antithrombotic agents of the invention have advantageous properties that make them preferable to the linearly multimeric peptides known in the art. In particular, the antithrombotic agents of the invention exhibit IC$_{50}$ values of platelet aggregation inhibition (i.e., the concentration of each agent at which platelet aggregation is reduced by 50%) lower than the IC$_{50}$ values for platelet aggregation inhibiting agents known in the art.

In addition, such multimeric polyvalent antithrombotic agents of the invention exhibit increased retention times at thrombus sites in vivo, as detected by technetium-99m (Tc-99m) scintigraphy. These results suggest that the multimeric polyvalent antithrombotic agents of the invention are capable of remaining in contact with thrombi or at sites of thrombus formation for longer times than compounds known in the art. This indicates that the multimeric polyvalent antithrombotic agents of this invention bind to platelets with higher avidity than compounds known in the art.

Polyvalent linking moieties provided by the invention are comprised of at least 2 linker functional groups capable of covalently bonding to platelet-specific moieties, including linear and cyclic peptides. Such functional groups include but are not limited to primary and secondary amines, hydroxyl groups, carboxylic acid groups and thiol reactive groups. Polyvalent linking moieties are comprised of preferably at least three functional groups capable of being covalently linked to platelet-specific moieties, including linear and cyclic peptides. Preferred polyvalent lining moieties include amino acids such as lysine, homolysine, ornithine, aspartic acid and glutamic acid; linear and cyclic amines and polyamines; polycarboxylic acids; activated thiols; and thiol-reactive reagents such as di- and tri-maleimides. Also preferred are embodiments wherein the polyvalent linking moieties comprise a multiplicity of polyvalent linking moieties covalently linked to form a branched polyvalent linking moiety. For the purposes of this invention, the term "branched" polyvalent lining moieties is intended to include but are not limited to polyvalent linking moieties having formula:

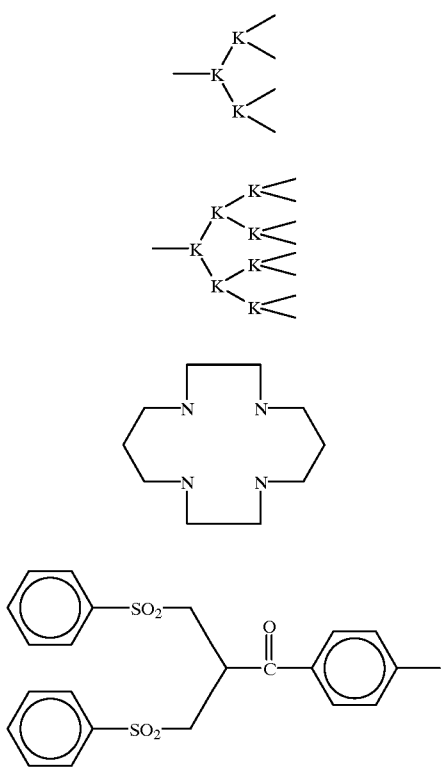

Most preferred polyvalent linking moieties include bis-succinimidylmethylether, tris(succinimidylethyl)amine and derivatives thereof.

Peptides of the present invention can be chemically synthesized in vitro. Peptides of the present invention can generally advantageously be prepared on an amino acid synthesizer.

The peptides provided by the invention are preferably administered intravenously in any conventional medium for intravenous injection such as an aqueous saline medium. Such medium may also contain conventional pharmaceutical adjunct materials such as, for example, pharmaceutically acceptable salts to adjust the osmotic pressure, buffers, preservatives and the like. Among the preferred media are normal saline and other isotonic buffers.

The antithrombotic agents of the invention, and methods for making and using these compounds, are more fully illustrated in the following Examples. These Examples illustrate certain aspects of the above-described invention and advantageous results thereof. These Examples are shown by way of illustration and not by way of limitation.

EXAMPLE 1

Synthesis of TMEA [tris(2-maleimidoethyl)amine]

tris(2-aminoethyl)amine (1.49 mL, 10 mmol) dissolved in 50 mL saturated aqueous sodium bicarbonate and cooled in an ice bath, was treated with N-carbomethoxymaleimide (4.808 g, 31 mmol). The mixture was stirred for 30 min on ice and then for another 30 mm at room temperature. The mixture was then partitioned between dichloromethane and water, dried over magnesium sulfate, filtered and evaporated to give 3.442 g of product. Reverse phase thin-layer chromatography (RP-TLC) yielded essentially 1 spot ($R_f$=0.63 in 1:1 acetonitrile:0.5M sodium chloride). 3.94 mmol (1.817g) of this product was dissolved in 20 mL tetrahydrofuran and 20 mL saturated sodium bicarbonate and mixed for 2 h. The reaction mixture was then partitioned between ethyl acetate and water. The organic phase was washed with saturated sodium chloride, dried over magnesium sulfate, and filtered. The ethyl acetate solution was diluted with hexanes and cooled. Solid TMEA was collected by filtration and dried to a yield of 832 mg. Chemical analysis of the product confirmed its identity as TMEA as follows:

$^1$H NMR (CDCl$_3$): 2.65 (tr. 2 H), 3.45 (tr.2 H). 6.64 (s. 2 H).

$^{13}$C NMR (CDCl$_3$), 35.5, 51.5, 133.9, 170.4.

EXAMPLE 2

Solid Phase Peptide Synthesis

Solid phase peptide synthesis (SPPS) was typically carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexyl-carbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethyl-phenoxymethylpolystyrene (HMP) resin for carboxyl-terminus acids or Rink amide resin for carboxyl-terminus amides. Resin-bound products were routinely cleaved using a solution containing trifluoroacetic acid (TFA) and various amounts of dichloromethane (DCM), water, thioanisole, ethanedithiol, and triethylsilane (TES), typically a solution of TFA:DCM:H$_2$O:TES, prepared in ratios of 50:50:5:2 for 0.5–1.5 h at room temperature.

Where appropriate, N-terminal acetyl groups were introduced by treating the free N-terminal amino peptide bound to the resin with 20% v/v acetic anhydride in N-methylpyrrolidinone (NMP) for 30 min. Where appropriate, 2-chloroacetyl or 2-bromoacetyl groups were introduced either by using the appropriate 2-haloacetic acid as the last residue to be coupled during SPPS, or by treating the N-terminus free amino acid peptide bound to the resin with either the 2-haloacetic acid/diisopropylcarbodiimide/N-hydroxysuccinimide in NMP or the 2-haloacetic anhydride/diisopropylethylamine in NMP.

Where appropriate, HPLC-purified 2-haloacetylated peptides were cyclized by stirring an 0.1–1.0 mg/mL solution in phosphate or bicarbonate buffer or ammonia solution (pH 8.0), which may also contain 0.5–1.0 mM EDTA, for 0.5–48 h followed by acidification with acetic acid, lyophilization and HPLC purification.

Where appropriate, TSEA adducts were prepared by reacting single thiol-containing peptides (1 to 10 mg/mL in aqueous buffer, pH 7, with or without added acetonitrile) with 0.33 molar equivalents of TMEA [tris(2-maleimidoethyl)amine] added in 0.2 to 1 mL dimethylformamine (DMF) at room temperature for approximately 1 to 2 hours. The products were purified by HPLC.

Where appropriate, BSME adducts were prepared by reacting single thiol-containing peptides (1 to 10 mg/mL in aqueous buffer, pH 7, with or without added acetonitrile) with 0.5 molar equivalents of BMME (bis-maleimidomethylether) pre-dissolved in DMF at room temperature for approximately 0.5 to 2 hours. The solution was concentrated and the product were purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS). Illustrative peptides are shown in Table I.

TABLE I

| Peptides | MWt* | HPLC** |
|---|---|---|
| (CH$_2$CO,Y$_D$,Apc,GDCGGC$_{Acm}$GC$_{Acm}$GGCamide)$_2$-BSME | 3021[1] | 12.4 |
| (CH$_2$CO,Y$_D$,Apc,GDCGGC$_{Acm}$GC$_{Acm}$GGCamide)$_3$-TSEA | 4563[2] | 12.8 |

*Molecular weight determined by 1: fast atom bombardment mass spectroscopy (MH$^+$) or 2: electrospray mass spectroscopy (M)
**HPLC methods [in R$_T$(min)]:

solvent A=0.1% CF3COOH/H$_2$O
solvent B$_{90}$=0.1% CF$_3$COOH/90% CH$_3$CN/H$_2$O
solvent flow rate=1 mL/min
Waters column=Waters DeltaPure RP-18, 5μ, 150 mm×3.9 mm analytical column
Conditions: 10% A to 40% B$_{90}$ in 20 min Single-letter abbreviations for amino acids can be found in G. Zubay, Biochemistry (2d. ed.), 1988 (MacMillen Publishing: New York) p.33; Acm=acetamidomethyl; Apc=L-[S-(3-aminopropyl)cysteine; Y$_D$=D-tyrosine; BSME=bis-succinimidylmethylether; TSEA=tris(succinimidylethyl)amine Peptides are linked to BSME or TSEA linkers via the free thiol moiety of the unprotected cysteine residue (C) in each peptide.

EXAMPLE 3

Platelet Aggregation Inhibition Assays

Platelet aggregation studies were performed essentially as described by Zucker (1989, Methods in Enzymol. 169: 117–133). Briefly, platelet aggregation was assayed with or without putative platelet aggregation inhibitory compounds using fresh human platelet-rich plasma, comprising 300,000 platelets per microliter. Platelet aggregation was induced by the addition of a solution of adenosine diphosphate to a final concentration of 15 micromolar, and the extent of platelet aggregation monitored using a Bio/Data aggregometer (Bio/Data Corp., Horsham, Pa.). The concentrations of platelet aggregation inhibitory compounds used were varied from 0.1 to 500 μg/mL. The concentration of inhibitor that reduced the extent of platelet aggregation by 50% (defined as the IC$_{50}$) was determined from plots of inhibitor concentration versus extent of platelet aggregation. An inhibition curve for peptide RGDS was determined for each batch of platelets tested as a positive control.

The results of these experiments are shown in Tables II and III. In Table II, the compounds tested are as follows (RGDS is given as a positive control):

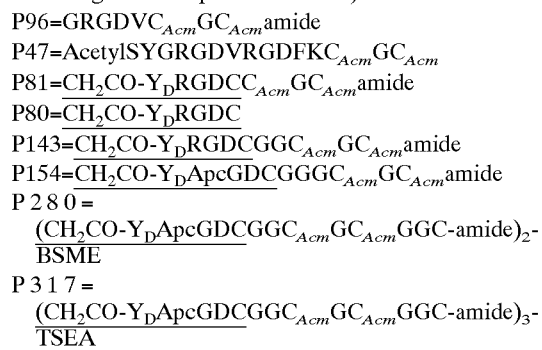

(Abbreviations used herein are the same as the abbreviations used in Table I).

These results demonstrate that the IC$_{50}$ decreases for cyclic peptides as compared with linear ones, and is even less for polyvalent peptide agents as compared with monovalent peptide agents. These results illustrate the efficacy of the multimeric polyvalent antithrombotic agents of the invention at reducing platelet aggregation.

Table III shows the IC$_{50}$ values of the agents of the invention compared with some of the most potent antithrombotic agents known in the prior art. The compounds tested as shown in Table III are as follows (RGDS is again given as a positive control):

Cytogen Pac-8=AcetylSYGRGDVRGDFKCTCCA
Monsanto=H$_2$NC(N═H)NH(CH$_2$)$_7$CO-GDF[1]
Rhone-Poulenc-Rorer=H$_2$NC(N═H)NH(CH$_2$)$_5$CO-Sar.DV[2]
Genentech=(1-naphthyl)CHCO-GRGDC[3]

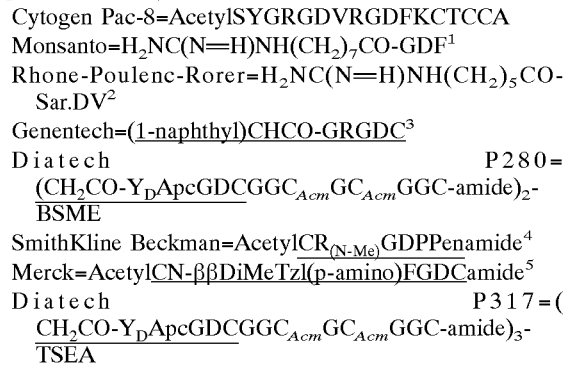

(Pen=L-penicillamine; Sar=sarcosine; other abbreviations are as in Table I. References for these peptides are all taken from the Proceedings of the 12th American Peptide Symposium, held in Cambridge, Mass. on Jun. 16–21, 1991: [1]: Tjoeng et al., Abst. LTh8; [2]: Klein et al., Abst. P-492; [3]: Burnier et al., Abst. LTh9; [4]: Ali et al., Abst. P-471; [5]: Nutt et al., Abst. LF11).

These results demonstrate that the multimeric polyvalent antithrombotic agents P280 and P317 provided by the invention have a capacity to inhibit platelet aggregation with efficiencies comparable to and in some cases better than the most potent peptides known in the prior art.

It should be understood that the foregoing disclosure emphasizes certain specific embodiments of the invention and that all modifications or alternatives equivalent thereto are within the spirit and scope of the invention as set forth in the appended claims.

TABLE II

INHIBITION OF PLATELET AGGREGATION

| Peptide | Type | IC$_{50}$ ($\mu$M) |
|---|---|---|
| RGDS | linear | 140 |
| P96 | linear, chelator | 121 |
| P47 | linear, dimer, chelator | 23 |
| P81 | cyclic, no spacer, chelator | 23 |
| P80 | cyclic, no chelator | 0.60 |
| P143 | cyclic, spacer, chelator | 1.3 |
| P154 | R analog, cyclic, spacer, chelator | 0.30 |
| P280 | R analog, cyclic, dimer, spacer, chelator | 0.087 |
| P317 | R analog, cyclic, trimer, spacer, chelator | 0.028 |

TABLE III

INHIBITION OF PLATELET AGGREGATION

| Peptide | IC$_{50}$ ($\mu$M) |
|---|---|
| RGDS | 160 |
| Cytogen Pac-8 | 12 |
| Monsanto | 1.6 |
| Rhone-Poulenc Rorer | 0.63 |
| Genentech | 0.15 |
| Diatech P280 | 0.087 |
| SmithKline Beckman | 0.08 |
| Diatech P317 | 0.028 |
| Merck | 0.022 |
| echistatin | 0.03 |

What we claim is:

1. A multimeric antithrombotic agent comprising:

(a) at least two copies of a platelet-binding moiety comprising a ligand for a platelet GPIIb/IIIa receptor; and (b) a polyvalent linking moiety which is covalently bonded to each platelet-binding moiety thereby linking the platelet-binding moieties;

wherein said agent has a molecular weight of less than about 20,000 daltons.

2. The agent of claim 1, wherein said polyvalent linking moiety comprises at least two identical functional groups, wherein each functional group is capable of covalently bonding to said platelet-binding moiety.

3. The agent of claim 2, wherein each of said functional groups is selected from the group consisting of a primary amine, a secondary amine, a hydroxyl group, a carboxylic acid group and a thiol-reactive group.

4. The agent of claim 1, wherein said polyvalent linking moiety comprises a a branched polyvalent linking moiety.

5. The agent of claim 1, wherein said polyvalent linking moiety is selected from the group consisting of bis-succinimidylmethylether, tris(succinimidylethyl)amine, a derivative of bis-succinimidylmethylether and a derivative of tris(succinimidylethyl)amine.

6. The agent of claim 1, wherein each platelet-binding moiety is covalently bonded to said polyvalent linking moiety by a functional group selected from the group consisting of a primary amine, a secondary amine, a hydroxyl group, a carboxy acid group and a thiol-reactive group.

7. A method for preventing thrombosis within a mammalian body comprising the step of administering an effective therapeutic amount of the agent of claim 1 in a pharmaceutical carrier.

* * * * *